United States Patent [19]

Roberts et al.

[11] Patent Number: 5,047,058
[45] Date of Patent: Sep. 10, 1991

[54] SYSTEM OF INSERTS FOR THE TIBIAL COMPONENT OF A KNEE PROSTHESIS

[75] Inventors: Jeffrey G. Roberts, Palm Harbor, Fla.; James A. Rand, Rochester, Minn.; Thomas Buford, III, Germantown, Tenn.; Jennifer J. Lackey, Memphis, Tenn.

[73] Assignees: Smith & Nephew Richards, Inc., Memphis, Tenn.; Mayo Foundation for Medical Education & Research, Olmsted County, Minn.

[21] Appl. No.: 512,833

[22] Filed: Apr. 23, 1990

Related U.S. Application Data

[63] Continuation of Ser. No. 179,428, Apr. 8, 1988, abandoned.

[51] Int. Cl.⁵ .......................... A61F 2/38; A61F 2/30
[52] U.S. Cl. ........................................ 623/20; 623/11; 623/16; 623/18

[58] Field of Search ...................... 623/11, 16, 18, 20, 623/22, 23

Primary Examiner—David J. Isabella
Assistant Examiner—Gina M. Gualtieri
Attorney, Agent, or Firm—Pravel, Gambrell, Hewitt, Kimball & Krieger

[57] ABSTRACT

A plurality of various shaped wedges, each wedge having an upper and lower face, each face including a plurality of spaced aligned protrusions adapted to engage a plurality of channels formed in the under surface of the tibial base, the protrusions registering with the channels to allow positioning of the wedge relative to the shape of the tibial component in various positions along the edge of the component, so that the plurality of wedges may be positioned to align themselves with the edge of the tibial component, and therefore in addition to providing a spacer between the bone and the undersurface of the component, to be secured within the same confined area as the component.

15 Claims, 3 Drawing Sheets

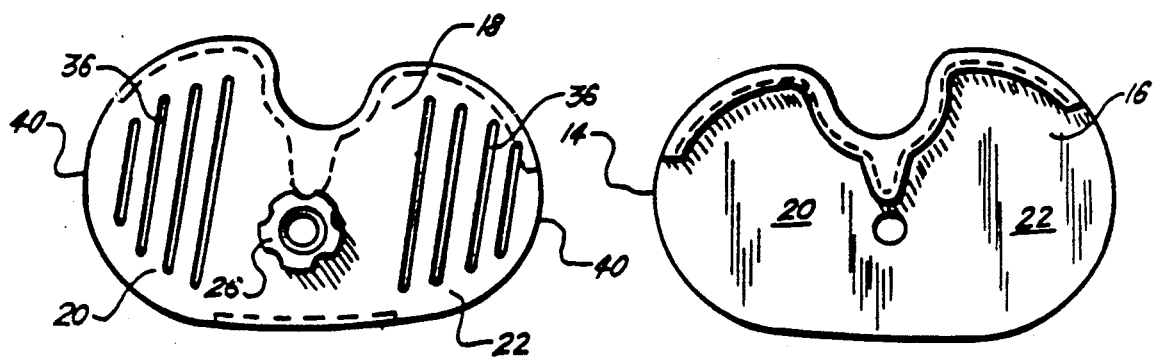
FIG. 1.   FIG. 2.
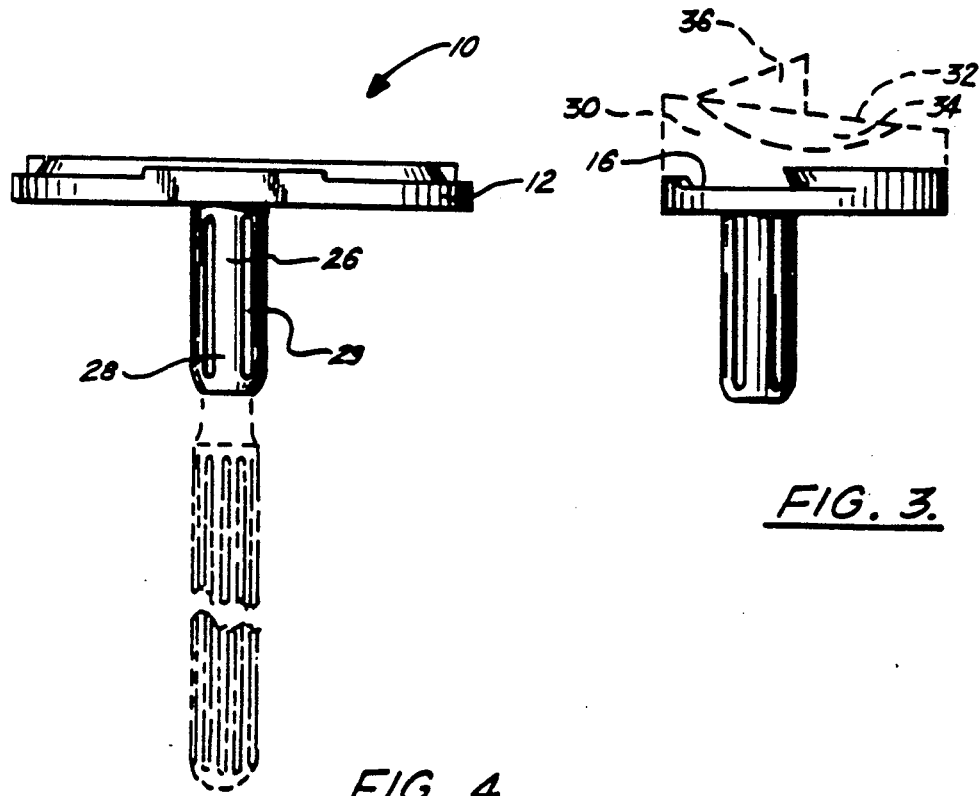
FIG. 3.
FIG. 4.

SYSTEM OF INSERTS FOR THE TIBIAL COMPONENT OF A KNEE PROSTHESIS

BACKGROUND OF THE INVENTION

This application is a continuation of U.S. patent application Ser. No. 179,428, filed Apr. 8, 1988 abandoned.

1. Field of the Invention

The present invention relates to knee prostheses. More particularly, the invention relates to a replacement system of the tibial component of a knee prosthesis which includes the use of inserts adapted to engage the undersurface of the tibial portion of the knee prosthesis to accommodate bony defects on the upper portion of the tibia.

2. General Background

In the total replacement of a knee joint, a knee prosthesis includes an upper femoral component which is a component secured to the upper femoral condyles that have been prepared and sculptured to secure the component in place. The second portion of the prosthetic knee includes a lower tibial component, which in a manner similar to that of the femoral component, is secured to the upper surface of a tibia that has been prepared to receive the tibial component. The third portion of the prothesis is a patella member which would be of common construction. The tibial component typically includes an upper platform or portion having a pair of concavities shaped to receive in nested relation the curved surfaces of a pair of condyle shaped segments formed on the femoral component in order to provide an articulation surface. These components are positioned and shaped to duplicate as closely as possible the natural bending movement of the knee. The lower portion of the tibial component is necessarily secured to the upper portion of the prepared tibia so as to provide a firm base of contact between the tibial component and the tibia.

In securing the tibial component to the upper portion of the tibia it is important that the overall condition of the hard outer bone layer of the tibia is able to support the weight of the body. In the course of surgery, as the tibia is being prepared to receive the tibial component, the tibia is typically sculptured to include a flat upper face so that a lower surface of the tibial component can rest on the tibia face with optional further attachment through a post member that fits into the medullary canal of the tibia. Bone cement may be used to secure the post to the tibia.

One problem that confronts surgeons during this type of procedure, is that oftentimes the outer surface of the hard bone on the tibia has eroded away. The extent of this may not be fully realized by X-rays or pre-surgery examination and thus the surgeon is not aware of the extent of the problem until surgery is underway. At this time, the surgeon must make critical decisions during a limited period of time and affix the tibial component to the prepared tibial portion. However, if the upper outer or inner portion of the tibia is soft or has eroded, proper spatial placement of the tibial component would cause a space to develop between the lower surface of the component and the upper surface of the tibia.

In order to correct this situation during the limited time available, surgeons have in the past improvised by positioning a sliver of bone or a bone graft or a portion of cement in order to fill the gap between the hard surface of the tibia and the undersurface of the tibial component. Although both of these alternatives provide some support to the tibial component, neither of them operates to firmly secure the tibial component in place. Another alternative is to resect additional bone to a level below the bony defect upon which the component can be mounted. This procedure is not preferred because in some cases a shortening of the tibia to a certain degree results in a corresponding shortening of that particular leg of the patient.

Therefore, a need has arisen for an acceptable insert positioned between the upper surface of the tibia that has been eroded away and the tibial component to avoid having to remove additional bone from the tibia, and to maintain the tibial component in the same anatomical position for maximum registration with the femoral component after the knee joint has been reconstructed.

SUMMARY OF THE PRESENT INVENTION

The present invention would provide a system of wedge-shaped spacer inserts which cooperate with the underside of the base of the tibial component and the upper portion of the tibia, when the tibia has eroded away and a space has developed or when a space is created after the removal of undesirable soft bone. This system comprises a plurality of various shaped inserts, each insert having an upper and lower face, each face including a plurality of spaced, aligned protrusions adapted to engage a plurality of channels formed in the under surface of the tibial base. The protrusions on the inserts register with the tibial base channels to allow positioning of the insert relative to the shape of the tibial component in various positions along the edge of the component so that the inserts are positioned to align themselves with the edge of the tibial component to provide a spacer between the bone and the undersurface of the component, which is secured within the same confined area as the component. In addition, due to the relative position of the projections on both faces of each insert, the same shaped insert may be utilized in either the left or right hemispheres of the tibial component. Therefore, the required configuration of inserts would be limited so that wedges in the left hemisphere would be moveable to the right hemisphere and therefore only require a minimum number of configured inserts for the surgeon to choose from during surgery.

Therefore, it is a principal object of the present invention to provide a tibial component system which enables the surgeon to correct bone erosion or bone softness confronted during implantation of the tibial component;

It is still a further object of the present invention to provide a tibial component replacement system into a limited number of inserts that can be utilized in both hemispheres of the tibial component to replace bone that has eroded or is removed away during surgery;

This summary of the invention is not intended to include all the aspects and advantages of this invention.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIGS. 1-4 are underside, plan, and side views respectively of the tibial base component of the apparatus of the present invention;

DETAILED DESCRIPTION OF THE PREFERRED EMBODIMENT

Figure 5:
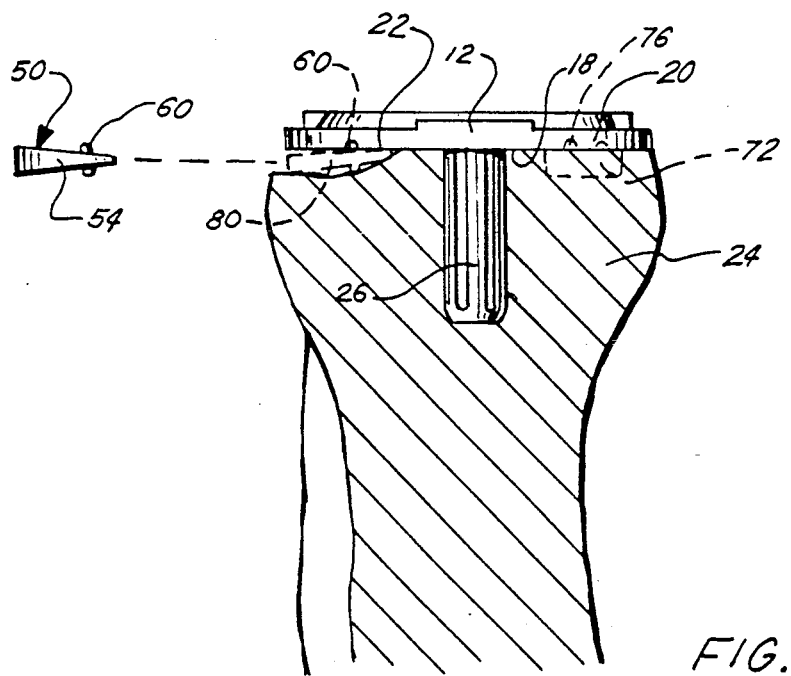
FIG. 5 is a partialy cross-sectional view of the tibial component mounted on a tibia in the preferred embodiment of the apparatus of the present invention.

The preferred embodiment of the system of the present invention is illustrated in the Figures, with FIGS. 1-4 illustrating in particular the tibial component 10. As seen in the Figures, tibial component 10 includes a flat, asymmetrically shaped base 12 having a superior flat face 16 and an inferior face surface 18, with base 12 substantially defining a left hemisphere 20, a right hemisphere 22, with the left hemisphere 20 and right hemisphere 22 substantially shaped to be received upon the pair of condyles of the lower tibia bone 24 as seen in FIG. 5. The base 12 has attached thereto a lower mounting member or shaft 26 having a plurality of ridges 28 along the length of mounting member 26, securable into the interior top portion of tibia 24, as further illustrated FIG. 5. In addition, as illustrated in FIG. 4, mounting member 26 may be adapted with an extension 27 frictionally engaged into a bore in member 26, to serve as an extension of member 26 for achieving a firmer mount between component base 12 and the condyles of tibia 24. For purposes of secure mounting, post 26 may be provided with cement in the grooves 29 defined between the ridges 28 so as to secure the base 12 in the inserted position.

In terms of function, in FIG. 3 there is illustrated in phantom view an upper tibial portion 30 which is mountable on the superior or upper surface 16 of base member 12, the platform 30 defining an upper sloping surface 32 and having a pair of oblong concavities 34 (only one of which is shown) for receiving condyler portions of the upper femoral component of the total knee prosthesis. For purposes of this application, the upper platform 30 of the tibial component is standard, and will not be discussed further.

As seen in FIG. 1, inferior or under surface 18 of tibial component base 12 is illustrated having post 26 extending inferiorly therefrom, and with left and right hemispheres 20 and 22 having a plurality of channels 36 in parallel relation, each of hemispheres 20 and 22 housing a series of four of said channels 36 with the length of the channels decreasing as the channels are positioned closer to the outer edge 40 of base portion 12. Therefore, when base portion 12 is positioned on the tibia as indicated in FIGURE 5, parallel channels 36 are positioned against the upper surface 25 of the tibia. The number of channels 36 may vary, and for purposes of explanation from channels 36 in each hemispheres 20 and 22 are noted.

Figure 6:
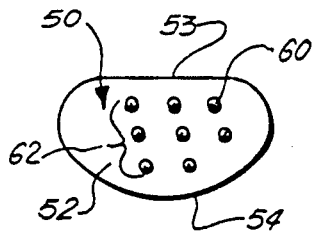
Figure 8:
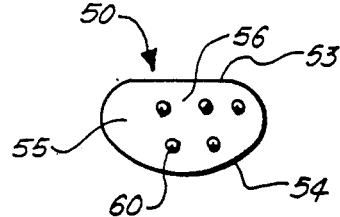
Figure 10:
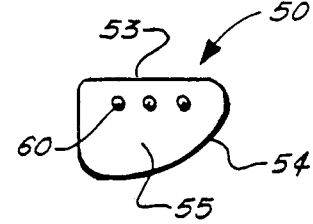

Turning now to FIGS. 6-13, a plurality of wedges of inserts 50 are depicted. In the embodiment illustrated, there are four principal types of inserts 50 which would be utilized in the present system. FIG. 6 illustrates in top view the largest of the inserts 52 which is generally oblong and has a first inner edge 53 and a continuous arcuate outer edge 54 which would conform substantially to the outer perimeter 40 of each hemisphere of tibial base 12 when the insert 52 is mounted in position intermediate the tibial bone 24 and the base 12 as seen in FIG. 5. FIG. 8 illustrates a smaller insert 56 which is substantially the same oblong shape of the larger insert 52 and thus has the same configured inner edge 53 and outer edge 54. FIG. 10 illustrates a substantially triangular shaped insert 58 which has an inner flat edge 53 and an arcuate outer edge 54 for aligning with the outer edge of base 12 upon implantation.

Figure 7:
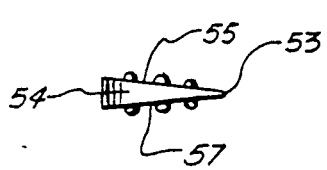
Figure 9:
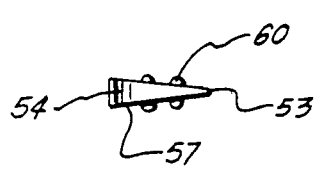
Figure 11:
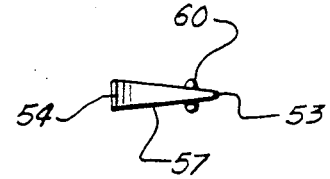

The profile construction of the inserts are illustrated in the FIGS. 7, 9, and 11. Each insert is wedge-shaped, having the substantially straight edge 53 at the thinnest or shallowest point in the wedge with the arcuate edge 54 constituting the thickest part of the insert to form the wedge shape as illustrated in FIGS. 7, 9, and 11. This particular arrangement is substantially identical to each of the types of wedges as illustrated.

A unique feature of the wedges 50 is that each includes a plurality of projections 60 which are placed in a particular configuration upon both the superior surface 55 and inferior surface 57 of each insert so that as illustrated in FIG. 6, the largest wedge 52 includes on each surface 55 and 57 three diagonal rows 62 across the width of the wedge. Each of the rows 62 is substantially in diagonal parallel relation, and is spaced apart from other rows so that each projection 60 would be positioned in a particular channel 36 as illustrated in FIGS. 14-17. Thus the rows 62 of projections on each insert extend generally from the inside edge 53 at an arcuate angle thereto to outside edge 54 and are positioned to align with the spaced channels 34 on the bottom face of the tibia base portion 12. The individual protrusions 60 are spaced equidistant from each other in each row 62 in order to form transverse rows approximately parallel to front edge 53.

Likewise, it should be noted in FIG. 8 that the smaller wedge 56 has a plurality of projections 60, although the number of projections are reduced from the large wedge 52 due to the reduced surface area of the surfaces 55 or 57. Likewise as illustrated in FIG. 10, triangular wedge 58 has a single row of projections 60 which would in effect be maintained in a single channel 36 along the inferior face 18 of base 12. The fourth principal wedge 72 of FIGS. 12-13 will be described later.

The various positioning of the inserts 50 on the inferior face 18 of tibial base component 12 are illustrated in FIGS. 14-17. For example, in FIG. 14, principal wedge 52 is positioned substantially in the hemisphere 20 with each of the three rows 62 of projections 60 aligned and registering in a channels 36, with the outer edge 54 in substantial alignment with the outer edge 40 of base member 12. Likewise, in that same Figure, smaller wedge 56 of FIG. 8-9 includes projections 60 registering within channels 36. However, in this particular alignment, unlike the wedge 52, which could be considered a straight alignment along the length of channels 36, wedge 56 has been substantially rotated approximately 45° so that the edge 54 is aligned with the edge 40 of the hemisphere 22, and allows the positioning of this particular wedge along a different segment of the hemisphere, which may be required should that particular area of the bone be eroded or removal during surgery. It is noticed that the rows 62 such as in the principal insert of FIG. 6 are spaced with the protrusions 60 an equidistant apart not only with a row 62 but also from a protrusion in an adjacent row to provide multiple positions of alignment with the grooves 36.

Figure 14:
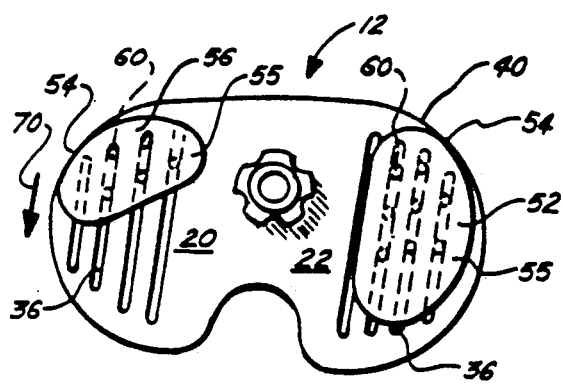
FIGS. 14-18 are various views of the inserts in various positions on the underside of the tibial component of the preferred embodiment of the present invention.
Figure 15:
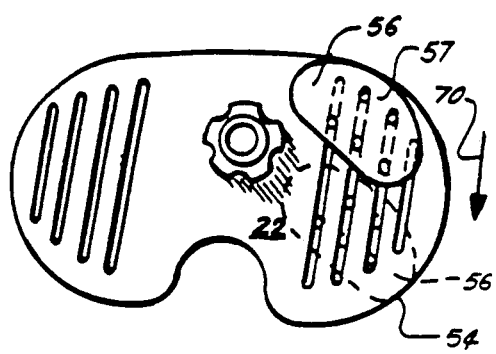

FIG. 15 illustrates the use of the wedge 56 positioned in hemisphere 20 similar in position to wedge 56 as illustrated in FIG. 14 as placed in hemisphere 22. This is accomplished by utilizing the series of projections 60 on the inferior face 57 of insert 56 when the insert is positioned in one hemisphere as compared to the other hemisphere. Therefore, there is a "mirror image" created in the utilization of the insert so that principal arcuate surface 54 is aligned with the outer edge 40 of hemisphere 20 in FIG. 15. Although it is not illustrated, like large wedge 52, smaller wedge 56 could likewise be placed in straight alignments within channels 36 in addition to the position illustrated in FIG. 15. Also, insert 56 can be slid or moved from the position as is illustrated in FIG. 15 along the direction of Arrow 70, to a position (phantom view) wherein the lower portion of arcuate edge 54 would align with the lower curved edge of hemisphere 20.

Figure 16:
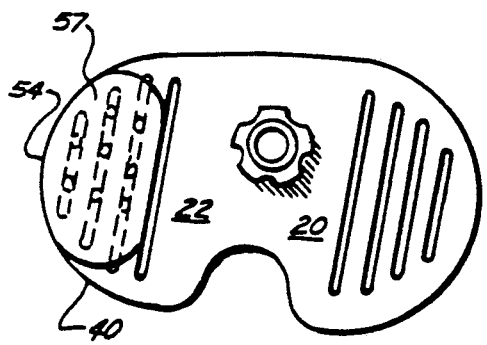

FIG. 16 illustrates large insert 52 having been moved from hemisphere 20 as shown in FIG. 14 to hemisphere 22. Therefore, this maneuverability of the inserts along the length and across the channels allows the placement of one or more of the wedges 50 to cover almost any erosion that may occur in the particular bone area with just allowing a few wedges to be utilized.

Figure 17:
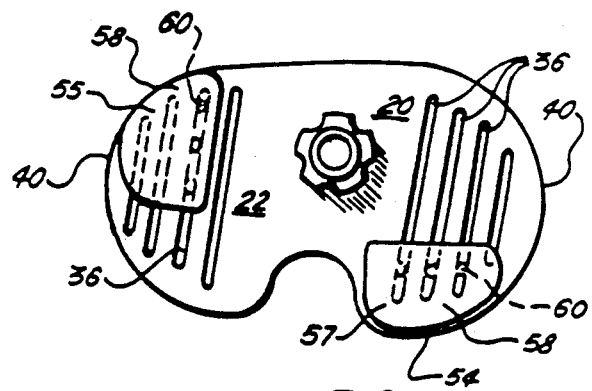

As illustrated in FIG. 17, generally triangular insert 58 of FIGS. 10-11, is utilized in hemisphere 22 in position with projections 60 registering with a single channel 36 with the arcuate edge 54 in alignment with the edge 40 of base 12. Also in that Figure, generally triangular wedge 58 of FIGS. 10-11 has been realigned in hemisphere 20 so that the projections 60 on inferior surface 57 have registered with three channels 36 and with the arcuate edge 54 of wedge 58 aligned with another point of the edge 40 of base 12 so that it may be utilized to cover a different area of an eroded bone.

Figure 12:
FIGS. 6-13 are views of the plurality of types of inserts used in the system of the present invention.
Figure 13:
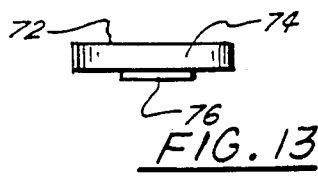
Figure 18:
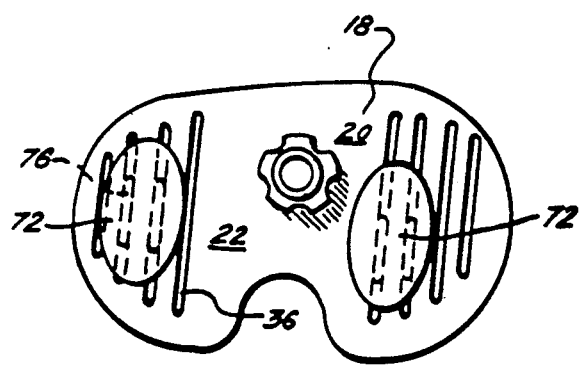

In addition to the three principal wedges as discussed, there is included a fourth insert 72 illustrated FIGS. 12 and 13 and in FIG. 18 mounted in position on the inferior surface 18 of base portion 12. As illustrated, insert 72 is is substantially oval shaped and has a uniform thickness along its edge 74. Rather than including a series of projections or protrusions 60, insert 72 includes a pair of raised, elongated projections or ridges 76 for registering with the pair of channels 36. For purposes of use, insert 72 would be utilized in substantially the central area of the tibia that may have eroded away, and is illustrated in phantom view in FIG. 5 to compensate for a rather large and deep area of the pulp of the bone that may have eroded away with insert 72 set in position within the pulp so as to provide additional support.

For purposes of illustration, reference is made to FIG. 5 where it is illustrated the base portion 12 of the tibial insert has been placed upon the upper surface of a tibia bone 24, with fixation post 26 inserted into the pulp of the bone. It is noted that a portion of the tibia 24 has eroded away or been removed substantially below hemisphere 22 of base portion 12, leaving an eroded space 80 between the upper portion of tibia bone 24 and the inferior surface 18 of component 12. Therefore, a typical insert 50, for example triangular insert 58 of FIGS. 10-11, would be placed into position between the upper portion of the eroded bone and the inferior surface 18 of component 12. The projections 60 are fitted into a single channel 36 in order to maintain insert 54 in position. In order to ensure further stability, insert 54 may be held in place via a bone cement which is common in the art. Therefore, once in place, insert 50 fills the void 80 created by the erosion or removal of bone, and therefore component 12 is maintained in fixed position atop tibia bone 24. Likewise, there is included in FIG. 5 a phantom view of oval insert 72, which is shown position substantially below hemisphere 20 of component 12 to fill a void in the pulp area of bone 24 which may have been created by erosion of pulp in the core of the bone. Therefore, insert 72 would be placed in the eroded portion with its elongated projections or ridges 76 likewise registering with channels 36 in the inferior surface of face 18 of component 12.

For purposes of illustration, the particular series of inserts as illustrated in the Figures, is merely elucidative, and the shape of the various inserts may vary according to the need of the surgeon during surgery. However, it has been found that this series of inserts 52, 56, and 58 provides practically complete coverage of erosion that may occur along the edge of the tibia, and therefore provides the surgeon with a small yet substantially complete selection of inserts that he may utilize during surgery when a problem such as this would arise.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A spacer system adapted to be inserted between an inferior contact surface of a prosthesis and adjacent bone, comprising:
   a) a component of a bone prosthesis including an inferior contact surface adapted to engage adjacent bone under normal bone conditions; and
   b) a spacer adapted to fill a void between at least a portion of said contact surface and adjacent bone, including a first surface to engage the prosthesis and a second surface to engage adjacent bone;
   c) the first surface of the spacer and contact surface of the prosthesis including a plurality of cooperating projections and receiving portions sized and shaped so the projections can register with the receiving portions in a plurality of locations so the spacer can be located at a selected one of a plurality of locations on the inferior contact surface of the prosthesis.

2. The spacer system of claim 1, wherein the component includes a superior face adapted to receive a tibial platform thereupon.

3. The spacer system in claim 1, wherein an inferior contact surface of the component includes at least one channel formed in said contact surface and the first surface of the spacer includes a plurality of projections projecting outwardly from the first surface of the spacer.

4. The spacer system in claim 1, wherein the component has a curved outer edge and said spacer includes an edge portion configured to align with a portion of the outer edge of the component.

5. The spacer system in claim 3, wherein the first and second surfaces each have a plurality of projections.

6. The component in claim 5, wherein the component inferior contact surface includes opposite sides and the first and second faces of the spacer have a similar array of projections so that the spacer may be positioned on either side of the component to allow interchangeability of the spacer between the two sides.

7. The spacer system in claim 1, wherein the component further includes a post member extending inferiorly of said inferior contact surface to provide support into the medullary-canal of the tibia bone.

8. The spacer system of claim 1, including:
one of the inferior contact surface of the component and the first surface having at least one groove formed therein and the other of said inferior contact surface and the spacer having a series of projections for positioning in the grooves to cause the component and spacer to be registered together.

9. The spacer system set forth in claim 5, wherein the spacer is wedge-shaped in cross-section.

10. The spacer system set forth in claim 5, wherein the first and second surfaces are convergent with respect to each other.

11. The spacer system set forth in claim 5, wherein the component has a curved outer edge and the spacer first and second surface are configured to a generally oblong shape and provides a curved edge portion alignable with a portion of the curved outer edge of the component.

12. The spacer system set forth in claim 5, wherein the component has a curved outer edge and the spacer first and second surface are configured to a generally triangular shape and provides a curved outer edge of the component.

13. The spacer system set forth in claim 5, wherein the component has a curved outer edge and the spacer first and second surface are configured to a generally oval shape and provides a curved edge portion alignable with a portion of the curved outer edge of the component.

14. A knee prosthesis comprising a tibial component said tibial component comprising:
a) a general base portion having a superior face and an inferior face and a generally curved outer edge portion, the inferior face positioned against the tibial bone, and including a plurality of substantially parallel channels therein;
b) a generally curved insert positionable between the upper face of a tibial bone and the inferior face of the base portion, the insert including a plurality of projections spaced apart a distance to register with the channels in the inferior face and having an outer edge with a portion thereof curved; and
c) the channels and projections being sized and shaped so the insert can register in various positions along the inferior face so that a portion of the edge of the insert may align with a portion of the edge of the base portion.

15. A knee prosthesis comprising tibial component said tibial component, comprising:
a) a base portion having a superior face and a inferior face, the inferior face positioned against an upper surface of a tibial bone, and including a series of substantially parallel channels; and the superior face for receiving a tibial platform,
b) a plurality of insert members insertable between the inferior face of the base portion and bone in the tibia bone, the inserts including means for registering with said channels of the base portion so that the inserts may be selectively positioned and secured at one of a plurality of predetermined and distinct positions in relation to the base portion, and providing alignment of the edge of the inserts with the edge of the bas portion.

* * * * *